United States Patent [19]

Dunmore

[11] Patent Number: 4,960,893

[45] Date of Patent: Oct. 2, 1990

[54] 7-BROMOMETHYL-5-HALO-8-HYDROXYQUINOLINE AND METHOD OF PREPARATION

[75] Inventor: Gordon C. Dunmore, Alberta, Canada

[73] Assignee: The Dow Chemical Company, Midland, Mich.

[21] Appl. No.: 272,152

[22] Filed: Nov. 16, 1988

Related U.S. Application Data

[63] Continuation of Ser. No. 77,356, Jul. 24, 1987, abandoned.

[51] Int. Cl.$^5$ .......................................... C07D 215/28
[52] U.S. Cl. ...................................... 546/179; 546/90; 546/180
[58] Field of Search ......................................... 546/179

[56] References Cited

U.S. PATENT DOCUMENTS

| | | | |
|---|---|---|---|
| 2,681,910 | 6/1954 | Burckhalter | 260/286 |
| 2,746,963 | 5/1956 | Burckhalter | 260/286 |
| 3,391,114 | 7/1968 | Schaefer et al. | 260/47 |
| 3,491,100 | 1/1970 | Schaefer et al. | 260/287 |
| 3,560,508 | 2/1971 | Ruhl et al. | 260/289 |
| 4,065,455 | 12/1977 | Mattison | 260/289 XA |
| 4,520,099 | 5/1985 | Akimura et al. | 430/613 |
| 4,631,177 | 12/1986 | Yotsuyanagi et al. | 423/112 |

FOREIGN PATENT DOCUMENTS 60-42234  3/1985  Japan .

OTHER PUBLICATIONS

Fernando et al., "Chemical Abstracts", vol. 51, 1957, Col. 5623b.
Zinner et al., "Reactions of Quinoline Derivatives with Formaldehyde", Arch Pharm., 291, No. 10, pp. 493–502 (1958).
Chem. Abstracts 3287a, vol. 71, 1969, p. 307, Swiss 465,958.
Chem. Abstracts 101:230364e, vol. 101, 1984, p. 755, JP 59,134,780.
Chem. Abstracts vol. 59, 1963, col. 7481, Ozawa et al., Yakugaku Zasshi 83, 498–502 (1963).
Chem. Abstracts vol. 60, 1964, Col. 10645-6, H. Fiedler, Arch. Pharm. 297(2), 108–117, 1964.
Derwent G6774, Jap. 15715/66.
Chem. Abstracts 3399z, vol. 80, 1974, p. 297, Fr. Demande 2,160,718.
Derwent 4099, Germ. 1,102,743.
Chem. Abstracts 100:220558m, vol. 100, 1984, p. 679, Uhlemann et al., Z. Anorg. Allg. Chem., 1984, 510, 79–87.
Chem. Abstracts 100:51428m, vol. 100, 1984, p. 567, Uhlemann et al., Z. Chem. 1983, 23(9), 334.
Derwent 11,681, Jap. 3843/64.
Chem. Abstracts 100:127563z, vol. 100, 1984, p. 410, Uhlemann et al., Anal. Chim. Acta 1984, 156,201-206.

*Primary Examiner*—Glennon H. Hollrah
*Assistant Examiner*—James H. Turnipseed
*Attorney, Agent, or Firm*—Paula Sanders Ruhr

[57] ABSTRACT

Halogenated hydroxyquinoline compounds such as 5-chloro-7-bromomethyl-8-hydroxyquinoline are prepared by contacting a 5-halo-8-hydroxyquinoline with formaldehyde to produce a cyclic dioxane and then contacting with concentrated hydrobromic acid to form the desired halogenated hydroxyquinoline compound.

The compounds of this invention are useful as intermediates in the production of ion-exchange resins.

14 Claims, No Drawings

7-BROMOMETHYL-5-HALO-8-HYDROXYQUINOLINE AND METHOD OF PREPARATION

CROSS-REFERENCE TO RELATED APPLICATION

This is a continuation of application Ser. No. 077,356, filed July 24, 1987, now abandoned.

BACKGROUND OF THE INVENTION

This invention relates to halogenated 8-hydroxy quinoline compounds and methods of their preparation.

Various substituted 8-hydroxyquinolines are known in the literature. For examples, see U.S. Pat. No. 3,491,100 to Schaefer et al., U.S. Pat. No. 3,560,508 to Ruhl et al., and U.S. Pat. No. 4,520,099 to Akimura et al. Generally, these compounds correspond to the formula

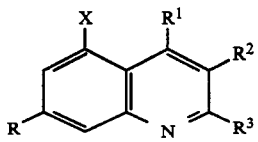

wherein X is halogen, preferably chlorine; $R^1$, $R^2$ and $R^3$ are independently hydrogen, lower alkyl such as methyl, ethyl, propyl and butyl, or other non-interfering substituents; and R has various definitions as will be discussed below.

Compounds of this general formula have varying utilities depending on the nature of the R substituent. In U.S. Pat. No. 2,746,963, R has the form

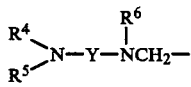

wherein $R^4$ and $R^5$ are independently in each occurrence alkyl or hydroxy radicals containing from 1 to 10 carbon atoms, or, when taken with

form a saturated heterocyclic radical such as piperidino; $R^6$ is hydrogen, methyl or ethyl; and Y is a divalent alkylene group of 2 to 5 carbon atoms. This results in a compound with therapeutic value, particularly against *Endameba histolytica*. In another patent, U.S. Pat. No. 4,520,099, R is preferably a second halogen atom and the compound has utility, when added to a silver halide emulsion layer, as photographic light-sensitive material in which aerial fog and spot fog are restrained. When R is a $C_{8-20}$ straight or branched chain alkyl or alkenyl radical, the resulting compound is disclosed to have utility as a reagent for the liquid ion-exchange extraction of some metals, especially copper or zinc. (U.S. Pat. No. 4,065,455).

The substituted 8-hydroxyquinolines are made in varying procedures depending on the type of substituents desired. The hydroxyquinolines disclosed in U.S. Pat. No. 2,746,963 are prepared by condensing a 5-chloro-8-hydroxyquinoline with formaldehyde and an amine in an alcoholic solvent preferably with heating. U.S. Pat. No. 3,491,100 to Schaefer et al. discloses the preparation of various substituted 8-hydroxyquinolines by the condensation of 8-hydroxyquinoline with N-methylol-α-halogen-acrylamides or N-methylol-1,2-dihalogeno-proprionamides. It is disclosed in U.S. Pat. No. 3,560,508 to Ruhl et al. to prepare dichloro-8-hydroxyquinolines in a process whereby 8-hydroxyquinoline is chlorinated in chloroform with excess chlorine in the presence of iodine. The 5-halo-7-alkenyl-8-hydroxyquinolines disclosed in U.S. Pat. No. 4,065,455 are prepared by reacting a 5-halo-8-hydroxyquinoline with an alkenyl chloride in the presence of sodium hydroxide and a dimethylsulfoxide solvent with heating. The 5-halo-7-alkyl-8-hydroxyquinolines also disclosed in U.S. Pat. No. 4,065,455 are prepared by reacting an 8-hydroxyquinoline with an alkenyl chloride as above with subsequent hydrogenation and halogenation.

While it is known how to prepare a number of substituted 8-hydroxyquinolines, a problem exists in that not all substituted 8-hydroxyquinolines can be prepared by these known methods. Further, it is desirable to produce novel compounds comprising 8-hydroxyquinolines with utility in the preparation of ion-exchange resins.

SUMMARY OF THE INVENTION

In one aspect, the present invention is a 5-halo-7-bromomethyl-8-hydroxyquinoline.

In another aspect, this invention is a process for the preparation of 5-halo-7-bromomethyl-8-hydroxyquinolines comprising contacting a 5-halo-8-hydroxyquinoline with formaldehyde in sulfuric acid to produce a cyclic dioxane derivative. The cyclic dioxane is then dissolved in concentrated hydrobromic acid to produce the desired 5-halo-7-bromomethyl-8-hydroxyquinoline.

In general, 8-hydroxyquinolines show great utility as intermediates and end products in the pharmaceutical and specialty chemical industries. The compounds of this invention are useful as intermediates in the preparation of 7-aminomethyl-8-hydroxyquinoline metal chelating ion-exchange resins.

DETAILED DESCRIPTION OF THE INVENTION

The compounds of the present invention are 5-halo-7-bromomethyl-8-hydroxyquinoline compounds wherein the hydroxyquinoline may be further substituted in the 2-, 3-, 4-, or 6- positions with an additional non-interfering substituent. For these purposes, a non-interfering substituent is one which does not interfere with the formation of the 5-halo-7-haloalkyl-8-hydroxyquinoline or with its use as an intermediate. Examples of non-interfering substituents include hydrocarbyl radicals, e.g., alkyl, methyl, ethyl and propyl, and aryl, such as phenyl.

In a preferred embodiment, the compounds of the present invention correspond to the formula

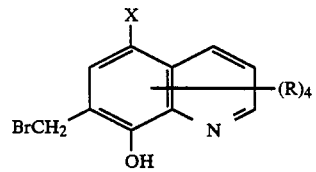

wherein X is chlorine, bromine or iodine: and, R is independently in each occurrence H or alkyl. It is preferred that R is independently in each occurrence H or lower alkyl. It is more preferred that X is chlorine and that R is hydrogen in each occurrence. It is most preferred that the compound is 5-chloro-7-bromomethyl-8-hydroxyquinoline.

The compounds of the present invention are prepared by a process wherein a 5-halo-8-hydroxyquinoline is reacted with formaldehyde in sulfuric acid to produce the cyclic dioxane derivative. The cyclic dioxane is in turn, in a novel process, dissolved in concentrated hydrobromic acid to produce the novel compounds of this invention. This process is summarized below.

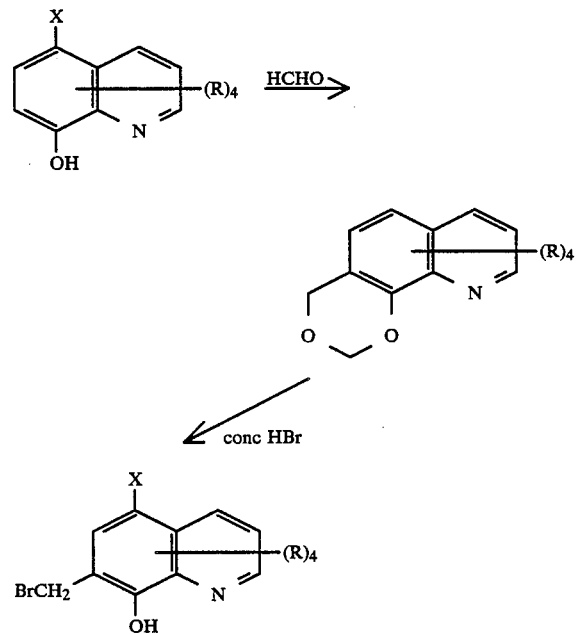

The starting materials used in the preparation of the novel compounds of this invention, 5-halo-8-hydroxyquinoline, are generally available commercially or may be prepared by one skilled in the art by the methods described in U.S. Pat. No. 4,065,455. It is also known to react 5-halo-8-hydroxyquinoline with formaldehyde in the presence of sulfuric acid to obtain 6-halo-4H-m-dioxino5,4-h]quinoline. (See, e.g., Zinner et al., Arch. Pharm., 291, 493–502 (1958).)

In a novel, one-step process, the cyclic dioxane is converted to the bromomethyl compound. The novel compounds so produced are characterized by elemental analysis and proton nuclear magnetic resonance.

In the one-step conversion from the cyclic dioxane to the bromomethyl compound, the dioxane is dissolved in concentrated hydrobromic acid. The resulting solution is heated and a bright yellow precipitate forms. After cooling, the product is isolated by conventional means such as filtration.

Any amount of concentrated hydrobromic acid which will dissolve the cyclic dioxane can be used in the practice of this invention. It is preferred that the ratio of hydrobromic acid to dioxane reactant be at least about 30:1 and no greater that about 45:1 on a weight to weight basis.

While additional solvents may be used, it is preferred that the concentrated hydrobromic acid act as solvent. Hydrobromic acid may be used at any concentration at which the reaction will proceed. It is preferred that the concentration of the HBr be at least about 40 percent. It is more preferred that the concentration of HBr should be close to saturation (about 48 percent w/w at 20° C.). The concentration of HBr may be maintained during the course of the reaction by adding HBr gas to the reaction mixture.

The conversion from the cyclic dioxane to the novel compounds of this invention may take place at any temperature at which the reaction will proceed. It is preferred to operate at a temperature of at least about 20° C. and at no greater than about 120° C. It is more preferred that the temperature be at least about 50° C. and no greater than about 100° C. It is most preferred that the temperature be at least about 80° C. and no greater than about 90° C. The reaction may take place at any pressure from atmospheric up to about 3,500 kPa absolute. It is preferred to conduct the reaction at about atmospheric pressure.

The reaction can proceed for any length of time until a satisfactory yield of at least about 75 percent based on the cyclic dioxane reactant is obtained. Preferred reaction times are from about fifteen minutes to about eight hours. A reaction time of about one to about four hours is more preferred. The process of this invention may be carried out in a batch mode or as a continuous process.

When the reaction is complete, the solution is cooled. It is preferred to cool the solution to between about 0° C. and 5° C. The product is then isolated as a hydrobromide salt by conventional means such as filtration.

The conversion of cyclic dioxane obtained by this process is at least about 90 percent and is preferred to be greater than about 98 percent. The selectivity to 5-halo-7-bromomethyl-8-hydroxyquinoline is at least about 90 percent and is preferred to be greater than about 98 percent. Minor losses are associated with the isolation of the product. It is preferred that these losses do not exceed about 20 percent. It is more preferred that these losses do not exceed about 15 percent. This results in an overall yield for this process of at least about 80 percent and preferably at least about 85 percent based on the cyclic dioxane reactant.

The novel compounds of this invention are useful in the preparation of ion-exchange resins. The preparation of these resins may be accomplished by conventional methods as, e. g., those described in Kirk Othmer, *Encyclopedia of Chemical Technology*, 3rd Edition, Volume 13, 678–705 (1981) which is hereby incorporated by reference.

SPECIFIC EMBODIMENTS

The following examples are given to further illustrate the invention and are not to be interpreted as limiting the invention in any way. Unless stated otherwise, all parts and percentages are given on a weight basis.

EXAMPLE 1

Preparation of 5-chloro-7-bromomethyl-8-hydroxyquinoline

A 32.0-g portion (0.14 mole) of 6-chloro-4H-m-dioxino[5,4-h]quinoline is prepared by reacting 5-chloro-8-hydroxyquinoline with formaldehyde in the presence of sulfuric acid by the procedure described by Zinner et al. in *Arch. Pharm.*, 291, 493–502 (1958) and is then dissolved in a reaction vessel containing 600 ml of 48 percent hydrobromic acid. The resulting solution is stirred and heated to about 85° C. After about 45 minutes, a bright yellow precipitate is noted. The temperature is maintained at about 85° C. for an additional two hours and 15 minutes. The solution is then cooled to between about 0° C. and 5° C. and the solid product is isolated by filtration through a fritted glass Buchner funnel. The product is washed with a small amount of ice-cold water, followed by ice-cold acetone. Forty-two grams (0.12 mole) of product is obtained representing a yield based on the dioxane reactant of about 86 percent. This yield represents conversion of the hydroxy quinoline and selectivity to the desired product of at least about 99 percent in each case. Some loss occurs in the isolation of the product.

The product is characterized by elemental analysis and shows the following:

|    | % Found | % Calculated |
|----|---------|--------------|
| C: | 34.18   | 33.98        |
| H: | 2.29    | 2.28         |
| N: | 3.96    | 3.96         |
| Cl: | 28.38  | 30.09        |

The product is also characterized by proton NMR (methanol -d4) and shows the following:

| 4.78 ppm | (s, 2H) |
| 5.08 ppm | (s, exch) |
| 7.99 ppm | (s, 1H) |
| 8.26 ppm | (dd, 1H, $J_{2,3}$ = 5.5 Hz, $J_{3,4}$ = 8.6 Hz) |
| 9.30 ppm | (m, 2H, $J_{2,4}$ = 1.4 Hz) |

These findings are consistent with the product being the hydrobromide salt of 5-chloro-7-bromomethyl-8-hydroxyquinoline.

EXAMPLE 2

Preparation of 7-Aminomethyl-5-chloro-8-hydroxyquinoline resin

A 5-ml portion of an aminomethylated resin is washed with methylene chloride to remove traces of water and is placed in a 250-ml 3-necked flask equipped with a condenser, solids addition funnel, thermometer and a stirring bar. The beads are swollen in methylene chloride overnight.

Sodium bicarbonate (1.48 g; 0.018 moles) and the hydrobromide salt of 5-chloro-7-bromomethyl-8-hydroxyquinoline (3.11 g; 0.009 moles) are thoroughly mixed with a mortar and pestle and added to the refluxing resin/methylene chloride slurry over a period of one hour. The beads change from white to yellow almost instantly and the mixture is then refluxed for 20 hours.

The resin is removed from the mother liquor by filtration and washed with 3N HCl/methanol (50/50) and then soaked in 1N NaOH for one hour. The resin is then refluxed in water/methanol (50/50) for one hour to remove the trapped, unreacted 8-hydroxyquinoline. This procedure is repeated twice. The green 7-aminomethyl-5-chloro-8-hydroxyquinoline resin is finally washed with 2 liters of deionized water. The product is characterized by infrared spectroscopy and elemental analysis.

What is claimed is:

1. A 5-halo-7-bromemethyl-8-hydroxyquinoline which corresponds to the formula

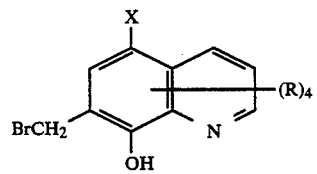

wherein X is chlorine, bromine or iodine; and R is independently in each occurrence H or alkyl.

2. The compound of claim 1 wherein X is chlorine.

3. The compound of claim 1 wherein R is hydrogen in each occurrence.

4. The compound of claim 1 which is 5-chloro-7-bromomethyl-8-hydroxyquinoline.

5. A process for the preparation of 5-halo-7-bromomethyl-8-hydroxyquinoline comprising contacting a 6-halo-4H-m-dioxino(5,4-h)quinoline with concentrated hydrobromic acid under reaction conditions sufficient to produce the 5-halo-7-bromomethyl-8-hydroxyquinoline.

6. The process of claim 5 wherein the concentration of the hydrobromic acid is at least about 40 percent on a weight to weight basis.

7. The process of claim 6 wherein the concentration of the hydrobromic acid is about 48 percent on a weight to weight basis.

8. The process of claim 5 wherein the weight ratio of hydrobromic acid to dioxane reactant is at least about 30:1 and no greater than about 45:1.

9. The process of claim 5 wherein the 6-halo-4H-m-dioxino(5,4-h)quinoline and the hydrobromic acid are contacted at a temperature between about 20° C. and 120° C.

10. The process of claim 9 wherein the 6-halo-4H-m-dioxino(5,4-h)quinoline and the hydrobromic acid are contacted at a temperature between about 50° C. and 100° C.

11. The process of claim 10 wherein the 6-halo-4H-m-dioxino(5,4-h)quinoline and the hydrobromic acid are contacted at a temperature between about 80° C. and 90° C.

12. The process of claim 5 wherein the conversion of 6-halo-4H-m-dioxino(5,4-h)quinoline is at least about 95 percent.

13. The process of claim 12 wherein the selectivity to 5-halo-7-bromomethyl-8-hydroxyquinoline is at least about 95 percent.

14. The process of claim 5 wherein the 5-halo-7-bromomethyl-8-hydroxyquinoline is obtained in a yield of at least about 85 percent.

* * * * *

UNITED STATES PATENT AND TRADEMARK OFFICE
CERTIFICATE OF CORRECTION

PATENT NO. : 4,960,893

DATED : October 2, 1990

INVENTOR(S) : Gordon G. Dunmore

It is certified that error appears in the above-identified patent and that said Letters Patent is hereby corrected as shown below:

On the title page, item [75] Inventor: "Gordon C. Dunmore" should correctly read --Gordon G. Dunmore--.

On the title page, item [57] Abstract, line 8, "usefual" should correctly read --useful--.

Column 2, line 67, "iodine:" should correctly read --iodine;--.

UNITED STATES PATENT AND TRADEMARK OFFICE
CERTIFICATE OF CORRECTION

PATENT NO. : 4,960,893

DATED : October 2, 1990

INVENTOR(S) : Gordon G. Dunmore

Page 2 of 4

It is certified that error appears in the above-identified patent and that said Letters Patent is hereby corrected as shown below:

Column 3, line 14 the process

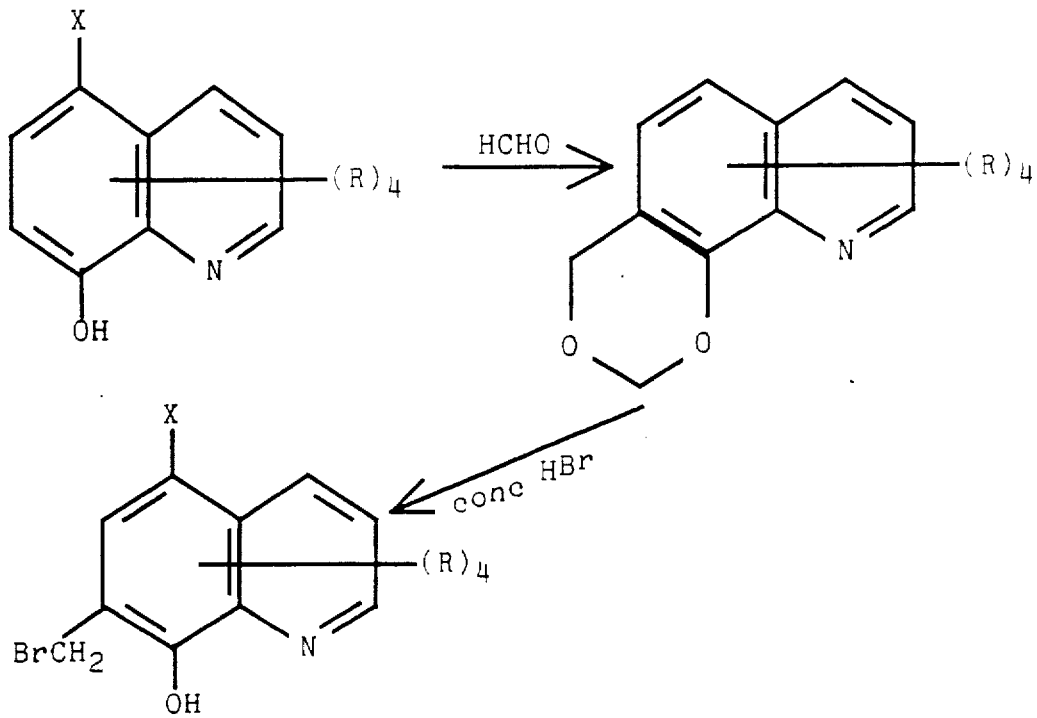

should correctly read --

UNITED STATES PATENT AND TRADEMARK OFFICE
CERTIFICATE OF CORRECTION

PATENT NO. : 4,960,893

DATED : October 2, 1990

INVENTOR(S) : Gordon G. Dunmore

Page 3 of 4

It is certified that error appears in the above-identified patent and that said Letters Patent is hereby corrected as shown below:

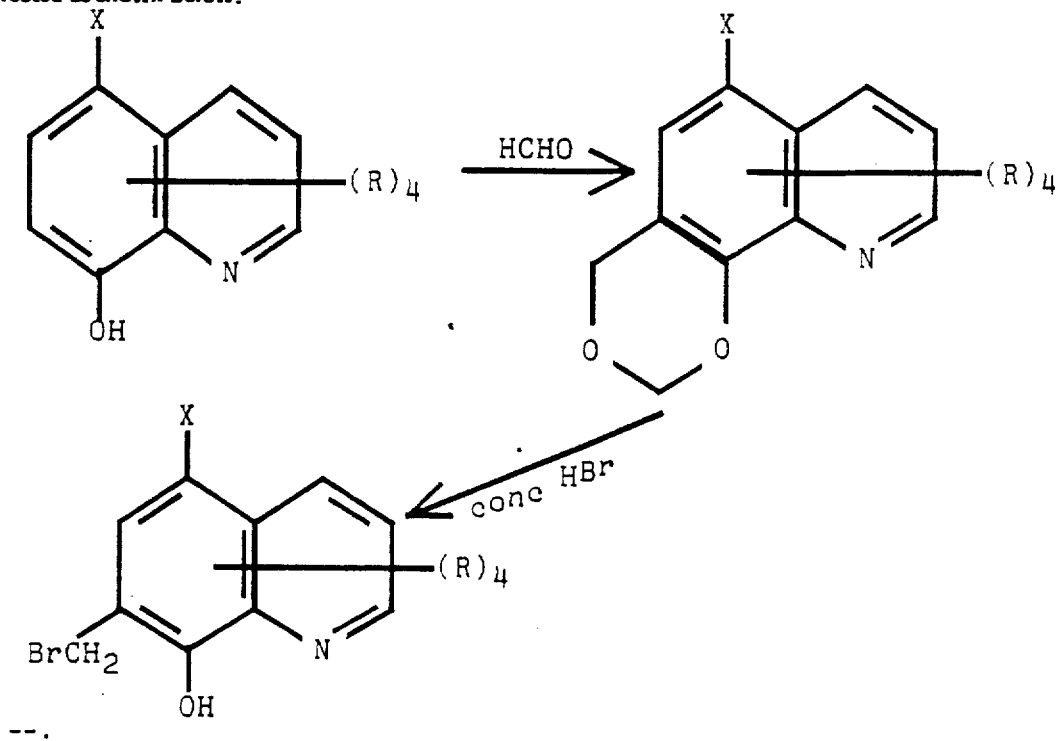

UNITED STATES PATENT AND TRADEMARK OFFICE
CERTIFICATE OF CORRECTION

PATENT NO. : 4,960,893

DATED : October 2, 1990

INVENTOR(S) : Gordon G. Dunmore

It is certified that error appears in the above-identified patent and that said Letters Patent is hereby corrected as shown below:

Column 3, line 46 "5,4-h]" should correctly read --[5,4-h]--.

Signed and Sealed this

Fourteenth Day of July, 1992

Attest:

DOUGLAS B. COMER

Attesting Officer

Acting Commissioner of Patents and Trademarks